United States Patent [19]
Gundolf

[11] Patent Number: 5,250,048
[45] Date of Patent: Oct. 5, 1993

[54] STABILIZING ELEMENT FOR OSTEOSYNTHESIS OF BONE FRAGMENTS, ESPECIALLY FOR THE FIXATION OF BONE FRACTURES

[76] Inventor: Ferdinand Gundolf, A46330 Kufstein, Austria

[21] Appl. No.: 826,074

[22] Filed: Jan. 27, 1992

[30] Foreign Application Priority Data

Jan. 28, 1991 [DE] Fed. Rep. of Germany ....... 4102462

[51] Int. Cl.5 .................................................. A01F 5/04
[52] U.S. Cl. ........................................ 606/69; 606/60
[58] Field of Search ........................ 606/69–72, 606/60; 602/5, 14, 17, 18, 19, 20, 21, 22, 23, 36

[56] References Cited

U.S. PATENT DOCUMENTS

| | | | |
|---|---|---|---|
| 1,916,789 | 7/1933 | Fordham | 602/5 |
| 1,950,799 | 3/1934 | Jones | 606/69 X |
| 2,966,907 | 1/1961 | Fasolino | 606/70 X |
| 3,710,789 | 1/1973 | Ersek | 606/69 X |
| 4,308,862 | 1/1982 | Kalmar | 602/14 |
| 4,583,541 | 4/1986 | Barry | 606/69 |
| 4,766,890 | 8/1988 | Hollrah | 602/14 |
| 4,898,160 | 2/1990 | Brownlee | 602/14 |

Primary Examiner—Robert A. Hafer
Assistant Examiner—Sam Rimell
Attorney, Agent, or Firm—Hale and Dorr

[57] ABSTRACT

The invention is directed to a stabilizing element for the osteosynthesis of bone fragments, especially for the fixation of bone fractures, said element at least partly covering the fracture and/or the bone in the area of the treated side and adapted to be fixed to the bone by at least one tension means.

16 Claims, 5 Drawing Sheets

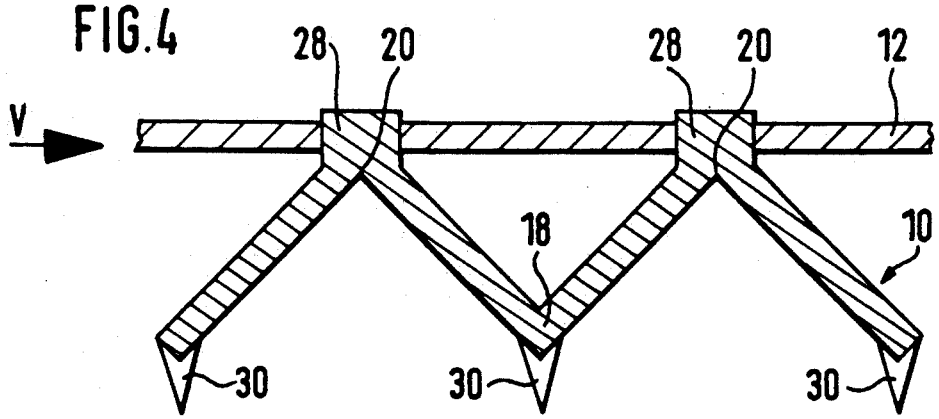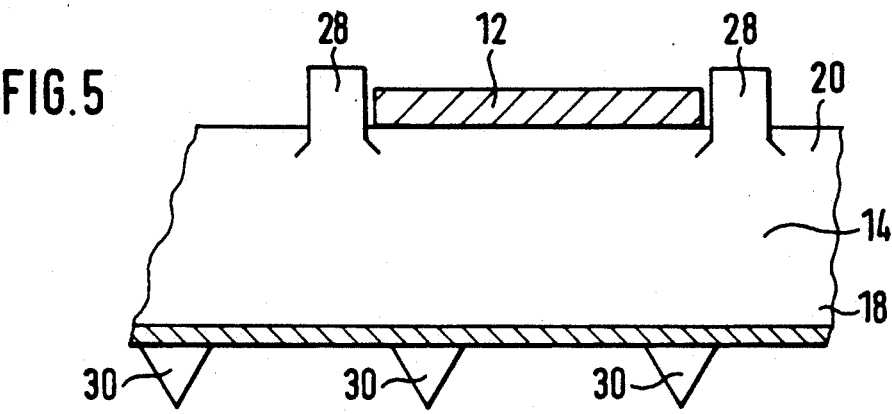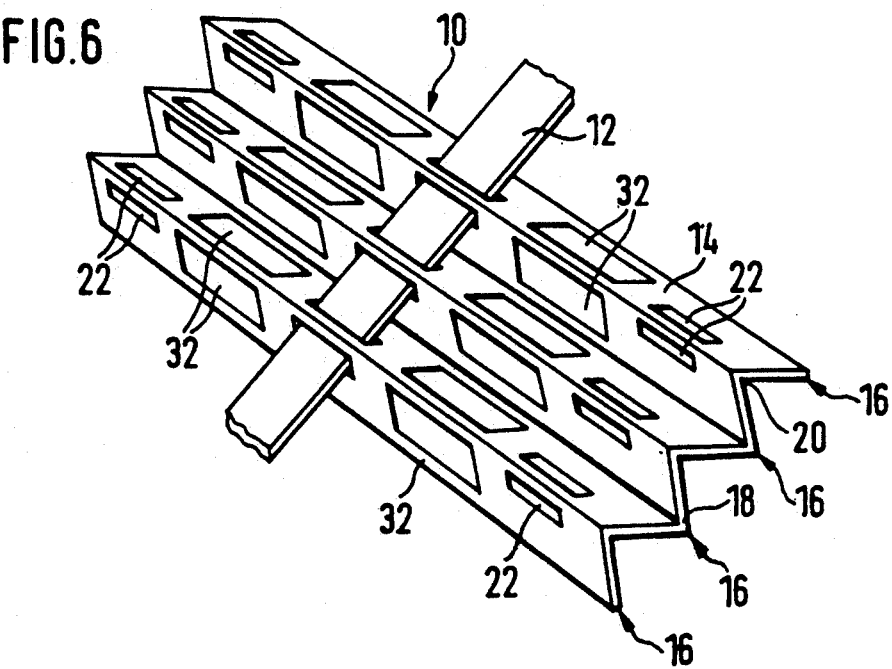

STABILIZING ELEMENT FOR OSTEOSYNTHESIS OF BONE FRAGMENTS, ESPECIALLY FOR THE FIXATION OF BONE FRACTURES

The instant invention is directed to a stabilizing element for the osteosynthesis of bone fragments, especially for the fixation of bone fractures, in accordance with the preamble of claim 1.

The chief aim in the treatment of a fracture is the restoration of the function of the injured limb. In order to prevent false positions and diseases of the fracture (ankylosis and soft-tissue injuries due to circulatory disorder) a stable osteosynthesis is to impart stability to the fractured bone whereby prolonged external fixation by plaster casts becomes unnecessary and an immediate active motion therapy of the injured limb is made possible. In the case of reparative operations on the skeletal system, the early active functional treatment is also a primary concern in addition to a reliable ossification. What is of further importance is a shortening of the stay in hospital, the restoration of the load-bearing capacity of the bone as quickly as possible, and above all the shortening of the operative procedure.

Stable osteosynthesis may be achieved, for instance, by interfragmentary compression acting on an area by means of traction screws. Furthermore, so-called axial compression has been known which may be achieved by the principle of traction straps, by two plates or by 2 to 4 Steinmann's pins which are fixed by means of external tension members. In addition to that intramedullary load-bearing members (intramedullary pins) are used, in which case the fracture is frequently stabilized additionally by a cerclage in the form of a special steel wire. Finally, the most varied shapes of compression plates and angular plates have been known which are removably joined to the bone by means of clamping screws and clips or the like.

However, all of these methods exhibit the drawback that they require a relatively high operative effort and that a more or less satisfactory stability of the fracture is achieved only with metal implants which have to be removed later. The normally used cerclages are moreover unsuited for holding fractures together in such a way that they exhibit their full load-bearing capacity. Also, the possible use of such cerclages is highly limited because for instance compression plates with clamping screws are unsuited for the fixation of old and/or porous bones and at least pose severe problems when used to achieve a firm fit. Apart from this, the treated bone as a whole is weakened by the provision of such plates, screws and the like. For instance, a screw passing through the bone represents a very likely predetermined break point. Finally, in the vicinity of the ends of conventional compression plates, angular plates or the like there occur additional stresses in the bone which will slow down the healing process, on the one hand, and on the other hand may result in relatively high loads acting on the bone in this area and possibly causing fracture of the bone.

Based on the above-specified prior art it is the object of the instant invention to provide a stabilizing element for the osteosynthesis of bone fragments, especially for the fixation of bone fractures, which is particularly easy to handle while it achieves high stability and good compatibility.

The specified object is solved by the characterizing features of claim 1.

Due to the wavy, meandering, staggered or similar profile or shape it is possible to obtain a stabilizing element having very high rigidity. Consequently, load-bearing element having as intramedullary pins are no longer required for the osteosynthesis of bone fragments, especially for the fixation of bone fractures. Moreover, due to the high rigidity obtainable by the profiling or shaping, the stabilizing element can be made much thinner than the heretofore known compression plates, angular plates and similar plates. The resulting good compatibility therefore also allows the stabilizing element of the instant invention to be retained when the bone has healed or the fracture has knit, respectively, so that a further operation for the purpose of removing intermedullary pins, compression plates, angular plates or other plate-like stabilizing auxiliary equipment will not be necessary. Due to the fact that the stabilizing element of the instant invention is supported by the bone along at least two lines of contact which extend approximately in the longitudinal direction of the stabilizing element, the rigidity or the stabilizing effect is additionally increased. Finally, the stabilizing element of the instant invention is very easy to handle and does not require any pre-operational matching steps for instance with the respective curvature of the bone in the area of the fracture, or the like.

The subclaims described structural details of the stabilizing element of the instant invention. The measures set out in claim 2 are highly important for a simple and quick as well as properly functioning fixing of the stabilizing element to the bone. Accordingly, the stabilizing element may be fixed to the bone by means of at least one flat tape-like tension band in the form of a pipe clamp or hose clamp, which serves as a tightening means and is wrapped around the fracture and/or the bone in the area of the treated location. In this connection reference shall expressly be made to the DE-PS 3,538,645 and the German Patent Application P 40 21 246.7. It has been found highly advantageous when the tightening means is provided as a tension band because irrespective of the consistency of the bone, i.e. also in the case of old, porous bones, the stabilizing element may be fixed thereto under compression, which is in contrast to conventional clamping screws.

Furthermore, the measures set out in claims 3 to 7 are of particular interest as regards very good handling and positioning or fitting of the tension band on the stabilizing element and hence on the bone. In particular, it is the fixing of the stabilizing element and the tension band or bands relative to each other by means of longitudinal slots, which are provided in the instant invention in accordance with the structural features of claims 5 to 7, which reliably prevents any undesirable mounting of the stabilizing element, any displacement of the tension band or bands along the stabilizing element, and the like.

In accordance with the features specified, it is also within the scope of the instant invention that in the vicinity of the lines of contact with the bone the stabilizing element is provided with sharp-edged, saw-tooth-like or similarly shaped projections which face the bone or the fracture, respectively. Any slippage or displacement of the stabilizing element and consequently of the tension band or bands either during the operation or subsequent thereto may be effectively prevented thereby. Additionally, in accordance with the structure measures specified in claim 8, the projections are asymmetrical, whereby in accordance with the instant invention the flank of each projection which faces the fracture is made to extend approximately normal to the stabilizing element while the flank of each projection which is remote from the fracture is made to extend towards the fracture at an inclination to the stabilizing element. This offers the special advantage that, when the projections penetrate the bone, a tractive effect away from the fracture and a compressive effect towards the fracture are additionally achieved, whereby the stabilization of bone and fracture by the stabilizing element of the instant invention is likewise promoted.

The embodiment of the instant invention as specified in claim 9 is intended to increase the rigidity of the bone or fracture-engaging stabilizing element in cooperation with the tension band or bands by causing an additional elastic prestressing. At the same time, any automatic loosening of the tension band due to lack of pre-stressing is counteracted thereby. The structure measure specified in claim 10 additionally promotes the elasticity of the stabilizing element as the result of a saving of material. Also, the compatibility of the stabilizing element of the instant invention is improved by reducing the amount of material. At the same time it is ensured that during the healing process the bone may grow through the stabilizing element, which may be a shaped honeycomb-type or perforated sheet metal member so that the bone may become an irremovable part thereof. Here, the arrangement of the instant invention as specified in claims 11 and 12 is advantageous and enables good compatibility.

A particular advantage is presented by the reinforcing strips provided on the stabilizing element as specified in claim 13, whereby the rigidity and especially the torsional rigidity or torsional strength of the stabilizing element is considerably increased even if the respective stabilizing element is provided with a large number of recesses in the form of round, square, rectangular, honeycomb or similar perforations. The reinforcing strips, which are particularly disposed in the vicinity of the edges facing the bone and/or the edges remote from the bone at the same time permit a reduction of the material thickness of the respective stabilizing element. In order to ensure that the lines of contact facing the bone will actually engage the bone, the reinforcing strips provided in the vicinity of the edges of the stabilizing element facing the bone will advantageously not protrude beyond the lines of contact.

Finally, the embodiment of the invention as specified in claims 14 and 15 additionally improves handling of the stabilizing element of the instant invention. Due to the weakened material or predetermined break points such as parting perforations, slots or the like it is possible, if required, during an operation to obtain correspondingly sized, i.e. sufficiently broad stabilizing elements by bending and subsequent breaking-off along the intended line of contact. In this way any difficult and frequently time-consuming preparatory measures for adapting the stabilizing element to the shape and size of the bone or fracture are eliminated. Also, in order to improve the handling of the stabilizing element of the instant invention, any reinforcing strips disposed thereon may also be provided with weakened material or predetermined break points in the form of parting perforations, slots or the like.

Further features, advantages and details of the invention will be apparent from the following description of some preferred embodiments of the invention and from the drawings, in which:

FIG. 4 is a partially broken-away cross-section of a further embodiment of a stabilizing element according to the invention corresponding to FIG. 2;

FIG. 5 is a partially broken-away side view of a stabilizing element according to FIG. 4 in the direction of the arrow V;

FIG. 6 is a perspective view of another embodiment of a stabilizing element according to the instant invention including a diagrammatic tension band;

Figure 1:
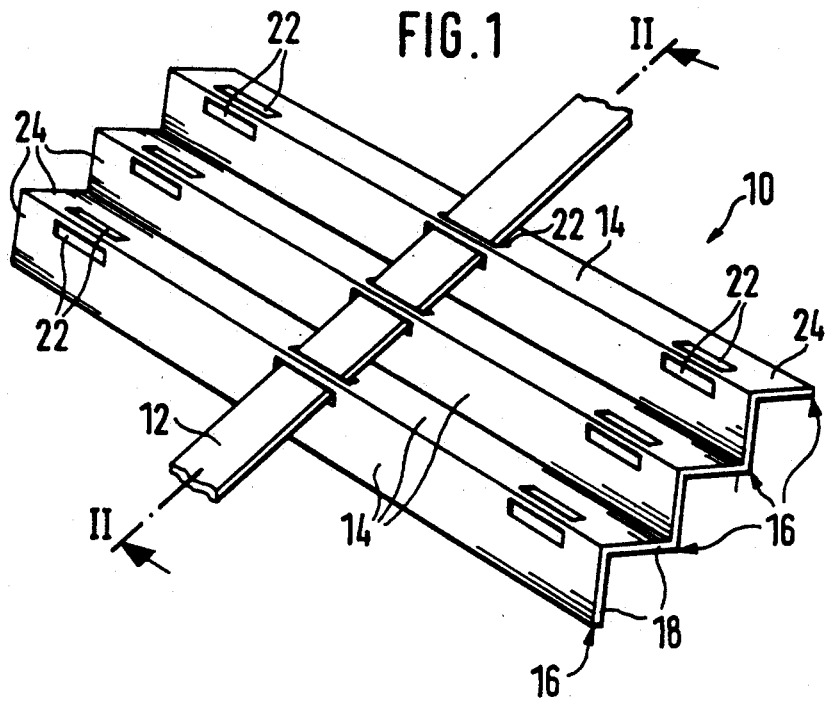
FIG. 1 is a perspective view of an embodiment of a stabilizing element according to the instant invention including a diagrammatic tension band.

FIG. 1 illustrates a stabilizing element for the osteosynthesis of bone fragments, especially for the fixation of bone fractures, which at least partially covers the fracture and/or the bone (not illustrated) in the region of the site to be treated and is fixed to the bone by at least one tightening means. The tightening means is configured like a pipe or hose clamp as a flat tape-like tension band 12 which is wrapped around the fracture and/or the bone in the area of the site to be treated. Function and structural design of the tension band 12, which is illustrated only partially and diagrammatically, correspond to the tension bands described in DE-PS 3,538,645 and in German Patent Application P 40 21 246.7.

Figure 2:
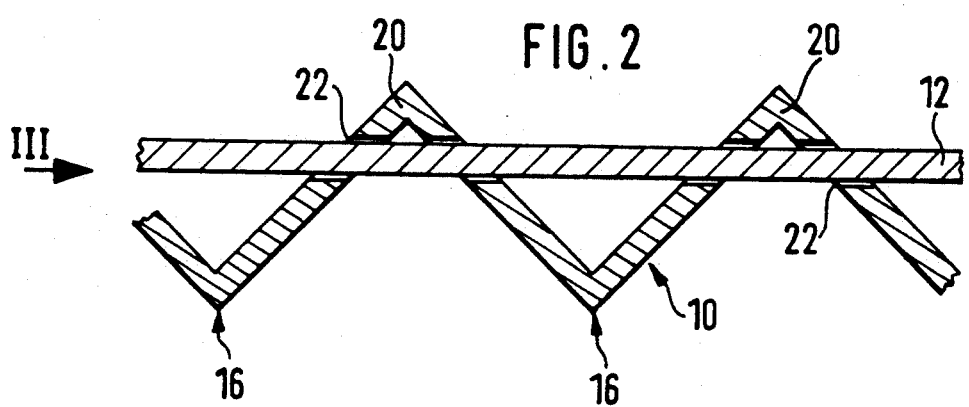
FIG. 2 is an enlarged, partially broken-away cross-section of the stabilizing element of FIG. 1 along the line II—II.

The stabilizing element 10 illustrated in FIGS. 1 and 2 has staggered or zigzag cross-section, wherein the dimensions of the individual surface portions or faces 14 of the stabilizing element 10 correspond to each other and the faces adjoin each other approximately at right angles. Due to this staggered profile the stabilizing element 10 acquires very high rigidity although the stabilizing element 10 is of comparatively small thickness. The stabilizing element 10 shown in FIG. 1 bears against the stabilizing element 10 shown in FIG. 1 bears against the bone (not illustrated) by way of four lines of contact 16 which extend substantially in longitudinal direction of the stabilizing element 10 and in the instant case are identical with the edges 18 of two respective adjoining faces 14 of the stabilizing element 10, said edges 18 facing the bone or fracture, respectively. In FIG. 2, the lines of contact 16 extend approximately normal to the plane of projection.

According to FIG. 2, the flat tape-type tension band 12 engages the stabilizing element 10 intermediate two respective adjoining lines of contact 16 at approximately equal distances from the lines of contact 16 and faces away from the bone (not illustrated). Therefore the stabilizing element 10 may be fixed to the bone under the desired selected compression with the aid of the tension band 12 wrapped about the bone while the bone itself need not be used for the fixation of the tension band 12. This offers the advantage that the stabilizing element 10 can quickly and simply be secured to the bone irrespective of the consistency of the fracture bone. In this respect the stabilizing element 10 is also particularly well suited for the treatment of old and frequently porous bones.

Figure 3:
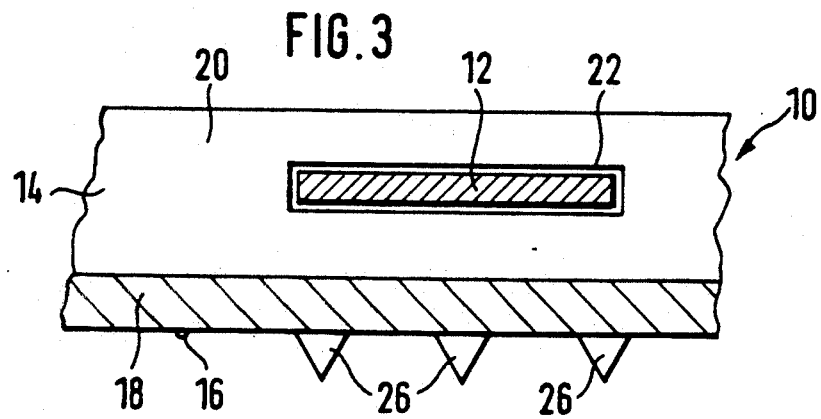
FIG. 3 is a partially broken-away side view of a slightly modified embodiment of a stabilizing element according to FIG. 2 in the direction of the arrow III.

As will be apparent from FIGS. 1 to 3 the stabilizing element 10 has bearing surfaces for positioning the tension band 12 or fixing the position of the tension band 12 relative to the stabilizing element 10. Any displacement or the like of the tension band 12 along the stabilizing element 10 during the operation and especially thereafter during the healing process is thereby prevented. The stabilizing element 10 is provided on at least one location, i.e. in the instant case between the edges 18 facing the bone and the edges 20 remote from the bone of two respective faces 14, with longitudinal slots 22 through which the tension band 12 may be passed so that it is correspondingly located relative to the stabilizing element 10 or the bone, respectively. Fixing of the stabilizing element 10 to the bone is further improved by the arrangement of longitudinal slots 22 in the end portions 24 of the faces 14 intended for located additional tension bands 12 not illustrated in FIG. 1. Also, the rigidity of the stabilizing element 10 can thereby be increased. The respective tension band 12 is accommodated practically without any play in the corresponding longitudinal slots 22 formed in the stabilizing element 10, because the free cross-section of the longitudinal slots 22 is dimensioned to be only slightly larger than the cross-section of such a tension band 12.

The embodiment of the stabilizing element 10 illustrated in FIG. 3 differs from that illustrated in FIGS. 1 and 2 by additionally provided projections 26 or the like which are disposed in the vicinity of the bone-engaging lines of contact 16 and project beyond the lines of contact 16 to face the bone or fracture, respectively. Due to the pointed or sharp-edged, especially sawtooth-like configuration of these projections 26, which necessarily penetrate the bone as the stabilizing element 10 is placed thereon and the tension band 12 is subsequently tightened, the stabilizing element 10 is additionally secured to the bone. Thus, any displacement of the stabilizing element 10 along the treated bone is reliably prevented by the projections 26. In the embodiment of the stabilizing element 10 shown in FIG. 3, the projections 26 are provided beneath the longitudinal slots 22 so that they are automatically urged into the bone as the tension band 12 is tightened.

In FIGS. 4 and 5 the bearing surfaces of the stabilizing element 10 for the tension band 12 are defined by two projections 28 or lugs or the like which are disposed according to the width of the tension band 12. The projections 28 protrude beyond the edges 20 of two respectively adjoining faces 4 of the stabilizing element 10 which face away from the bone, the clear height of said projections being slightly greater than the height of the respective tension band 12. The bearing surfaces configured as projections 28 offer the additional advantage of very simple mounting of the tension band 12 on the stabilizing element 10 during the operation. Also, the embodiment of the stabilizing element 10 illustrated in FIGS. 4 and 5 is provided with pointed or sharp-edged projections 30 which are presented to the bone and/or the fracture and are regularly spaced from each other along the lines of contact 16 on the edges 18 of the stabilizing element 10 which face the bone. The projections 30 of two respective adjacent lines of contact 16 may as well be additionally arranged in offset relationship.

FIG. 6 illustrates another embodiment of the stabilizing element 10, in which recesses 32 are formed in the faces 14 between the longitudinal slots 22. The recesses 32 promote the compatibility of the stabilizing element 10 due to a further reduction of material, on the one hand, and the fixing of the relative position of the stabilizing element 10 on the bone, on the other hand, because the bone may grow through the stabilizing element 10 in the course of the healing process.

Figure 7:
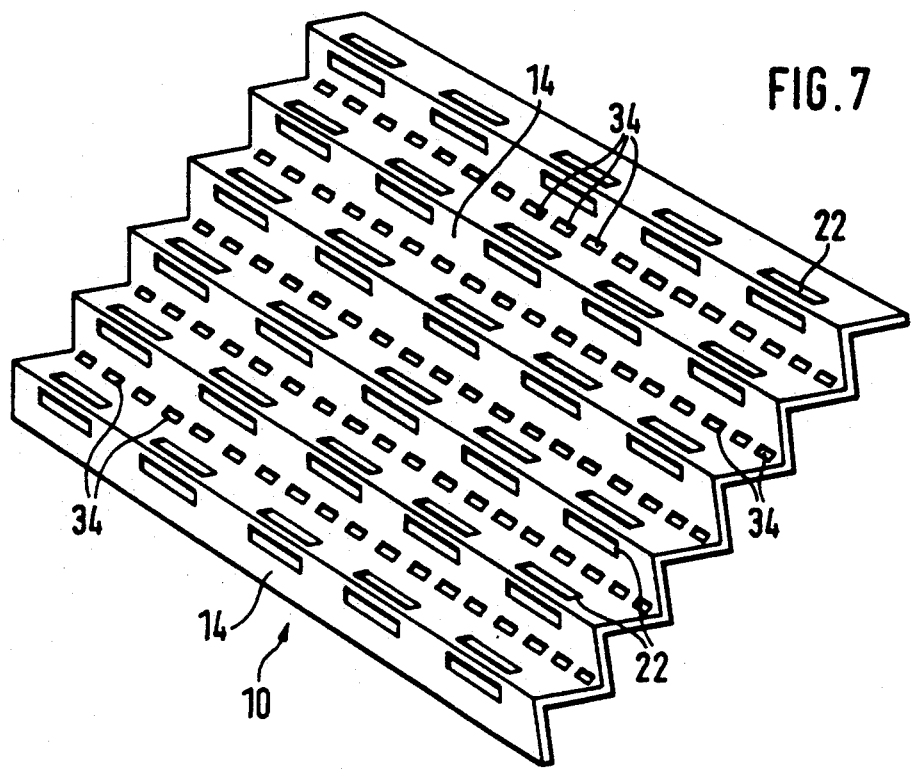
FIGS. 7 to 9 are perspective views of further embodiments of a stabilizing element according to the instant invention.
Figure 8:
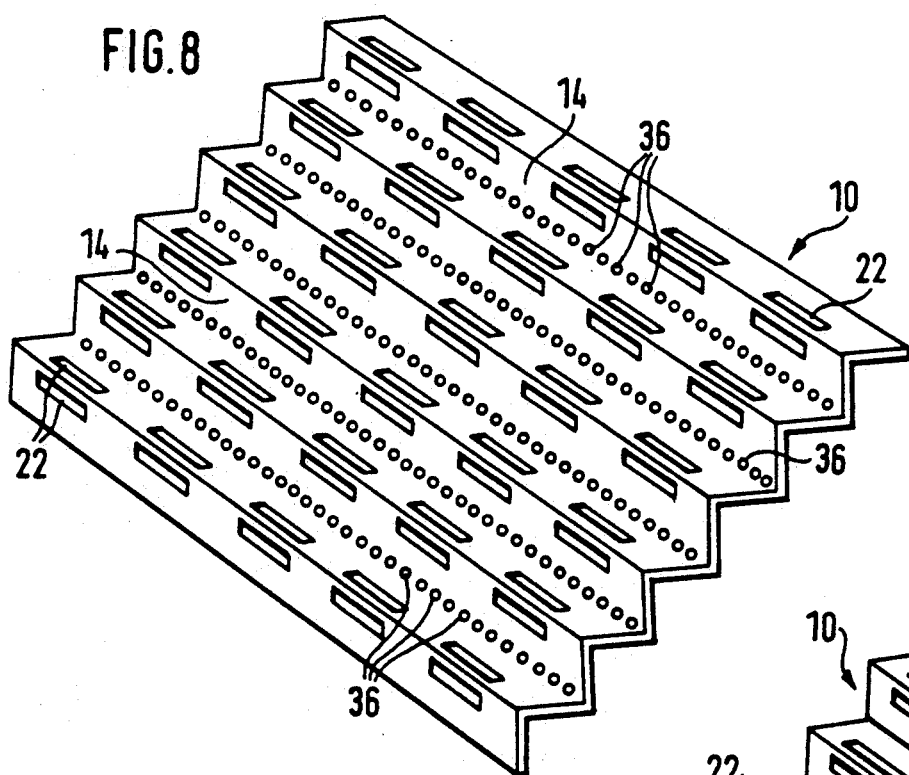
Figure 9:
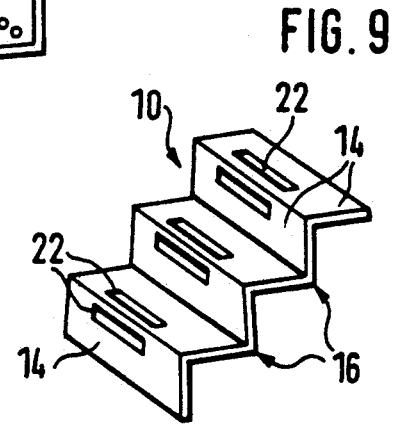
Figure 10:
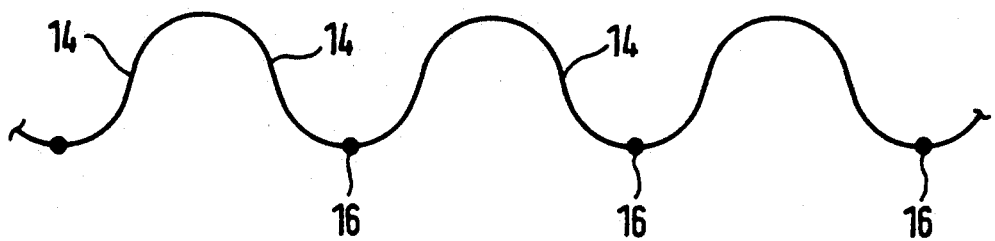
FIGS. 10 to 14 are diagrammatic cross-sections of further embodiments of stabilizing elements according to the instant invention.
Figure 11:
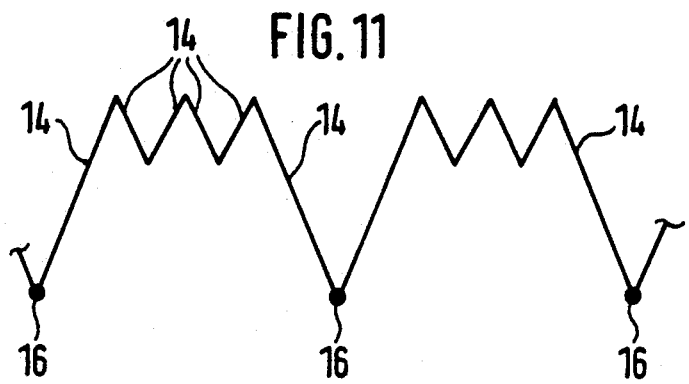
Figure 12:
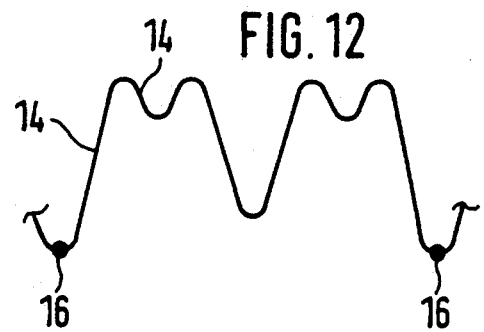
Figure 13:
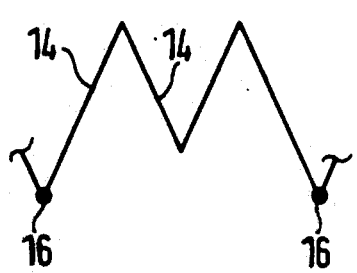
Figure 14:
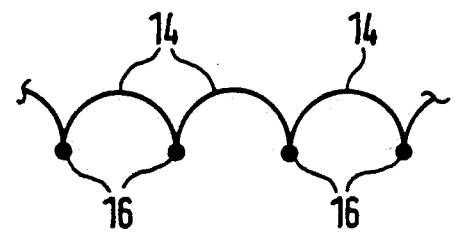

In the embodiments illustrated in FIGS. 7 and 8 the material of the stabilizing element 10 is weakened in the vicinity of, or preferably along, the lines of contact 16 engaging the bone. Thus, the stabilizing elements 10 shown in FIGS. 7 and 8 are provided with predetermined break points, especially in the form of parting slots 34 or parting perforations 36, respectively. In this way it is possible to adapt this size, i.e. the width of the stabilizing element 10 without any major preparations and at short notice to the treated location of the bone or fracture during an operation, and that quickly and without any major effort by bending along the respective line of contact 16, resulting in the breaking-off of the stabilizing element 10. Apart from this feature both the manufacture and the storage of this stabilizing element 10, which is similar to a modular system, are highly advantageous. The length of the stabilizing element may be varied as required. The stabilizing element illustrated in FIG. 9 is extremely short so that each individual face 14 has only a single longitudinal slot 22.

In FIGS. 10 to 14 further embodiments of the stabilizing element 10 are illustrated diagrammatically, and the shapes thereof are wavy (see FIGS. 10, 14), meandering (see FIG. 12) as well as of varying staggered configuration (see FIGS. 11, 13) or configured in a similar way. In all of these embodiments of the stabilizing element 10 the lines of contact 16, which are indicated by dots in FIGS. 10 to 14, are normal to the plane of the drawing. In accordance with the choice of the respective shape of the stabilizing element 10 it is possible to influence the rigidity thereof, because each profile is adapted to be brought into engagement with the bone or fracture under an inherent elastic stress.

Figure 15:
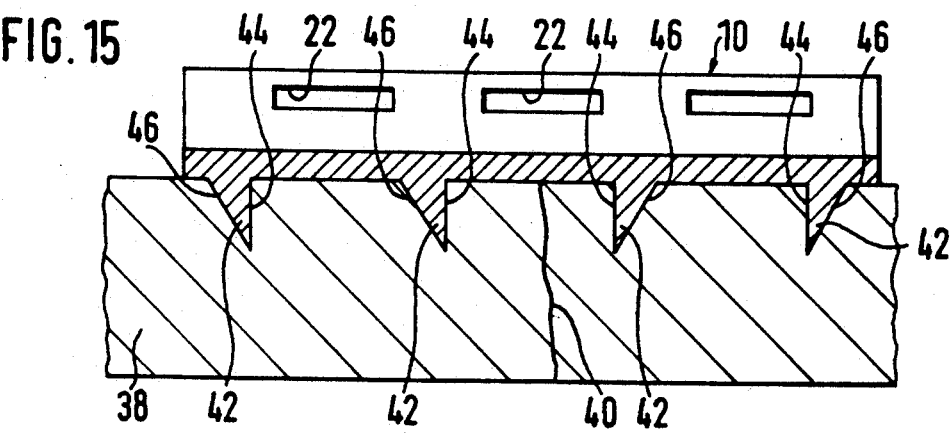
FIG. 15 is a reduced longitudinal sectional view corresponding to FIG. 3 of a further embodiment of a stabilizing element according to the instant invention in the area of a bone fracture.

FIG. 15 illustrates a further embodiment of a stabilizing element 10 of the instant invention which is in engagement with the bone 38 and covers the fracture 40. The pointed or sharp-edged, especially saw-tooth-like projections 42 which face the bone 38 are of asymmetric configuration. On the one hand, the flank 44 of each projection 42 facing the fracture is configured to extend approximately normal to the stabilizing element 10. On the other hand, the flank 46 of each projection 42 facing away from the fracture 40 extends toward the fracture 40 at an inclination to the stabilizing element 10. This offers the advantage that the projections penetrate the bone 38 as the tension band is tightened while applying a compressive force to the bone 38 in the direction of the fracture 40 or applying a corresponding tension to the stabilizing element in the longitudinal direction thereof. The result is that the two individual portions of the fractured bone are additionally urged against one another in the area of the fracture whereby in the final analysis the healing process is additionally promoted.

Figure 17:
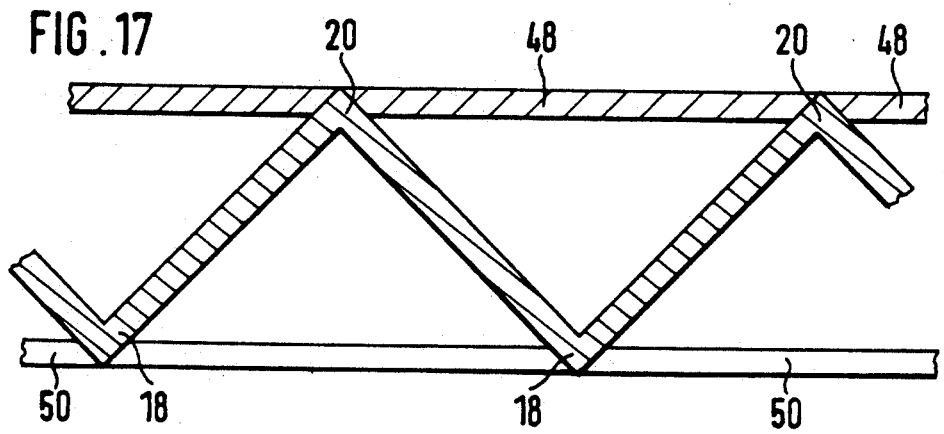
FIG. 17 is an enlarged, partially broken-away cross-section of the stabilizing element according to FIG. 16 along the line XVII—XVII.
Figure 16:
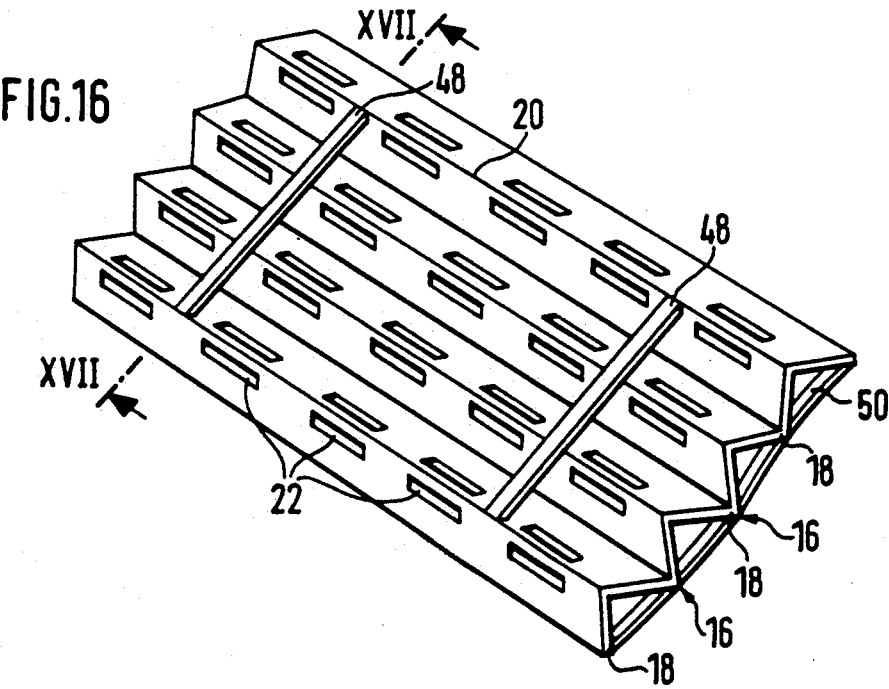
FIG. 16 is a perspective view of another embodiment of a stabilizing element according to FIG. 1.

FIGS. 16 and 17 illustrate another embodiment of the stabilizing element 10 which is provided with a plurality of reinforcing strips 48, 50 extending substantially across the longitudinal direction of the stabilizing element 10. The reinforcing strips 48 are disposed in the vicinity of the edges 20 of the stabilizing element which face away from the bone. In contrast thereto, the reinforcing strips 50 are disposed in the vicinity of the edges 18 which face the bone. It is preferred that the reinforcing strips 50 should not protrude beyond the lines of contact 16 which face the bone or fracture, whereby it is ensured that the lines of contact 16 themselves engage the bone and are held away therefrom because of protruding reinforcing strips 50. The reinforcing strips 48, 50 impart a substantially higher rigidity to the respective stabilizing element 10. Especially, the torsional rigidity or torsional strength of the stabilizing element 10 is increased by these reinforcing strips 48, 50. Correspondingly, the reinforcing strips 48, 50 may also be disposed at another location of the stabilizing element 10 intermediate two adjacent edges 18, 20 facing the bone and facing away therefrom, respectively. At the same time the stabilizing element 10, i.e. the faces 14 thereof, can have reduced material thickness on account of the obtainable increased rigidity, which in turn improves the compatibility of this stabilizing element 10. Finally, the reinforcing strips 48, 50 may be provided with weakened material portions or predetermined break points mainly in the vicinity of the edges 18, 20, particularly in the form of parting slots or parting perforations (not illustrated), whereby the handling of the stabilizing element is improved. In this respect it is possible to adapt the size, i.e. the width of the stabilizing element 10 by simple bending and breaking-off. In this respect the material thickness, the material width and cross-sectional shape of the reinforcing strips 48, 50 can be selected as desired.

Finally, the choice of material of the stabilizing element 10 depends on the special requirements or surgical demands made in each individual case. The stabilizing element 10 may be formed of implant material, especially metallic implant material such as titanium, or it may be made of ceramic material, plastics and other biologically compatible materials. It is likewise possible to form the stabilizing element of bone-like material, especially of hydroxyapatite, which is autolytic and/or through which the bone may grow.

The instant invention is not limited to the illustrated embodiments thereof. For instance, the previously described embodiments of the stabilizing element 10 may be combined in any desired way as regards their structural configuration and the arrangement of various technical features such as the projections 26, 28, 30, the recesses 32, the parting slots and perforations 34, 36, the number of longitudinal slots 22 and many other features. Furthermore, the sectional shapes of the stabilizing element 10 may also be varied as desired. Finally, the geometrical dimensions of the various sectional shapes may be varied in any desired way. For instance, the thickness of the faces 14 provided between two respective adjacent lines of contact 16 (see especially FIGS. 10 to 14) may be selected to be different. It is likewise conceivable that two or more separate stabilizing elements 10 of different lengths are disposed about the bone and may be fixed thereon with a single tension band.

All of the features disclosed in the instant application papers are claimed as being essential to the invention provided they are novel over the prior art either individually or in combination.

What is claimed is:

1. A stabilizing element for osteosynthesis of bone fragments, especially for the fixation of bone fractures, said stabilizing element comprising:
    at least one tension means; and
    an elongated member for at least partly covering the bone in the vicinity of the site to be treated, said elongated member having a wavy cross-section across a width of the elongated member and sharp-edged projections in the vicinity of the bone-engaging lines of contact whereby said projections would face the bone when the stabilizing element is in use, said elongated member being adapted to bear against the bone by an application of force from said at least one tension means along at least two lines of contact which extend approximately in a longitudinal direction of the stabilizing element, said longitudinal direction being substantially perpendicular to said width.

2. The stabilizing element as claimed in claim 1, wherein the elongated member is adapted to be fixed to the bone by means of at least one flat tape-like tension band in the form of a pipe or hose clamp, said tension band serving as said tension means and being wrapped around the elongated member.

3. The stabilizing element as claimed in claim 2, wherein the elongated member is provided with engaging surfaces for positioning the tension band.

4. The stabilizing element as claimed in claim 3, wherein the engaging surfaces for the tension band are defined by two projections which are disposed at a distance corresponding to the width of the tension band.

5. The stabilizing element as claimed in claim 3, wherein the elongated member further comprises at least on a portion thereof longitudinal slots through which the tension band may be passed.

6. The stabilizing element as claimed in claim 5, wherein the elongated member further comprises at least two longitudinal slots at the ends thereof through which tension bands may be passed.

7. The stabilizing element as claimed in claim 5 wherein a cross-section of the longitudinal slots formed in the elongated member is dimensioned to be slightly larger than the cross-section of the tension band.

8. The stabilizing element as claimed in claim 1, wherein the sharp-edged projections are asymmetrical, and wherein the flank adapted to face the fracture extends approximately normal to the elongated member while the flank adapted to face away from the fracture extends towards the fracture at an inclination to the elongated member.

9. The stabilizing element as claimed in claim 1, wherein the elongated member is adapted to be brought into engagement with the bone under elastic stress.

10. The stabilizing element as claimed in claim 1, wherein the elongated member further comprises recesses disposed intermediate the lines of contact.

11. The stabilizing element as claimed in claim 1, wherein the elongated member is formed of a material suitable for human implants.

12. The stabilizing element as claimed in claim 1, wherein the elongated member comprises a material having a hardness substantially the same as bone and which will disintegrate over time.

13. The stabilizing element as claim in claim 1, wherein the stabilizing element further comprises at least one reinforcing strip which extends substantially across the longitudinal direction of the elongated member and is especially disposed in the vicinity of the edges adapted to face the bone or the edges adapted to face away from the bone, wherein the reinforcing strips in the vicinity of the bone-facing edges preferably do not protrude beyond the lines of contact.

14. The stabilizing element as claimed in claim 1, wherein the material of the elongated member is weaker in the vicinity of the bone-engaging lines of contact.

15. The stabilizing element as claimed in claim 14, wherein along the lines of contact the elongated member is provided with predetermined break points, especially with, parting perforations.

16. The stabilizing element as claimed in claim 1 wherein the elongated member comprises a material having a hardness substantially the same as bone through which bone may grow.

* * * * *